(12) United States Patent
Sharma et al.

(10) Patent No.: US 8,617,522 B2
(45) Date of Patent: Dec. 31, 2013

(54) MULTIMODAL NANOPARTICLES FOR NON-INVASIVE BIO-IMAGING

(71) Applicant: University of Florida Research Foundation, Inc., Gainesville, FL (US)

(72) Inventors: Parvesh Sharma, Gainesville, FL (US); Brij M. Moudgil, Gainesville, FL (US); Glenn A. Walter, Newberry, FL (US); Stephen R. Grobmyer, Shaker Heights, OH (US); Swadeshmukul Santra, Orlando, FL (US); Huabei Jiang, Gainesville, FL (US); Scott Chang Brown, Hockessin, DE (US); Edward W. Scott, Gainesville, FL (US); Qizhi Zhang, Gainesville, FL (US); Niclas Bengtsson, Lake Forest Park, WA (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 0 days.

(21) Appl. No.: 13/729,815

(22) Filed: Dec. 28, 2012

(65) Prior Publication Data

US 2013/0129633 A1 May 23, 2013

Related U.S. Application Data

(62) Division of application No. 12/675,633, filed as application No. PCT/US2008/074630 on Aug. 28, 2008, now Pat. No. 8,361,437.

(60) Provisional application No. 60/968,476, filed on Aug. 28, 2007.

(51) Int. Cl.
*A61K 49/04* (2006.01)
*A61K 49/00* (2006.01)
*A61B 5/055* (2006.01)
*A61N 5/00* (2006.01)

(52) U.S. Cl.
USPC ........... 424/9.42; 424/9.2; 424/9.32; 424/9.6; 600/411; 600/431

(58) Field of Classification Search
None
See application file for complete search history.

(56) References Cited

U.S. PATENT DOCUMENTS

| | | | |
|---|---|---|---|
| 2006/0204754 A1* | 9/2006 | Kang | 428/379 |
| 2007/0026069 A1* | 2/2007 | Shastri et al. | 424/486 |
| 2007/0140974 A1* | 6/2007 | Torres et al. | 424/9.323 |
| 2007/0196281 A1* | 8/2007 | Jin et al. | 424/9.34 |

FOREIGN PATENT DOCUMENTS

| | | | |
|---|---|---|---|
| JP | 2000314576 A | * | 11/2000 |
| WO | WO 9727801 A1 | * | 8/1997 |

OTHER PUBLICATIONS

Wang et al. Photoacoustic tomography of a nanoshell contrast agent in the in vivo rat brain. 2004 Nano Lett. 4: 1689-1692.*
Veiseh et al. Optical and MRI multifunctional nanoprobe for targeting gliomas. 2005 Nano Lett. 5: 1003-1008.*
Santra et al. Synthesis and characterization of fluorescent, radio-opaque, and paramagnetic silica nanoparticles for multimodal bioimaging applications. 2005 Adv. Mater. 17: 2165-2169.*
Graf et al. Metallodielectric colloidal core-shell particles for photonic applications. 2002 Langmuir 18: 524-534.*
Loo et al. Immunotargeted nanoshells for integrated cancer imaging and therapy. 2005 Nano Lett. 5: 709-711.*
Salgueiriño-Maceira et al. Bifunctional gold-coated magnetic silica spheres. 2006 Chem. Mater. 18: 2701-2706. Published online May 9, 2006.*
Westcott et al. Formation and adsorption of clusters of gold nanoparticles onto functionalized silica nanoparticle surfaces. 1998 Langmuir 14: 5396-5401.*
Chi et al. Co oxidation over gold nanocatalyst confined in mesoporous silica. 2005 Appl. Catal. A Gen. 284: 199-206.*

* cited by examiner

*Primary Examiner* — Michael G Hartley
*Assistant Examiner* — Jennifer Lamberski
(74) *Attorney, Agent, or Firm* — Saliwanchik, Lloyd & Eisenschenk

(57) ABSTRACT

Multimodal nanoparticles are nanoparticles containing contrast agents for PAT and one or more of luminescence imaging, x-ray imaging, and/or MRI. The multimodal nanoparticles can have a dielectric core comprising an oxide with a metal coating on the core. The particles can be metal speckled. The multimodal nanoparticles can be used for therapeutic purposes such as ablation of tumors or by neutron capture in addition to use as contrast agents for imaging.

5 Claims, 13 Drawing Sheets

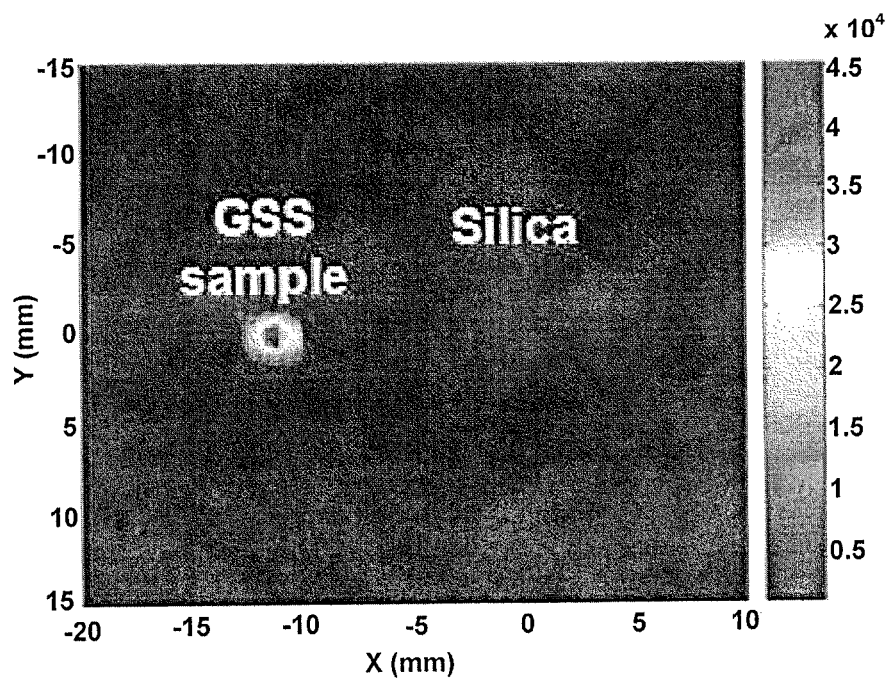
FIG. 3
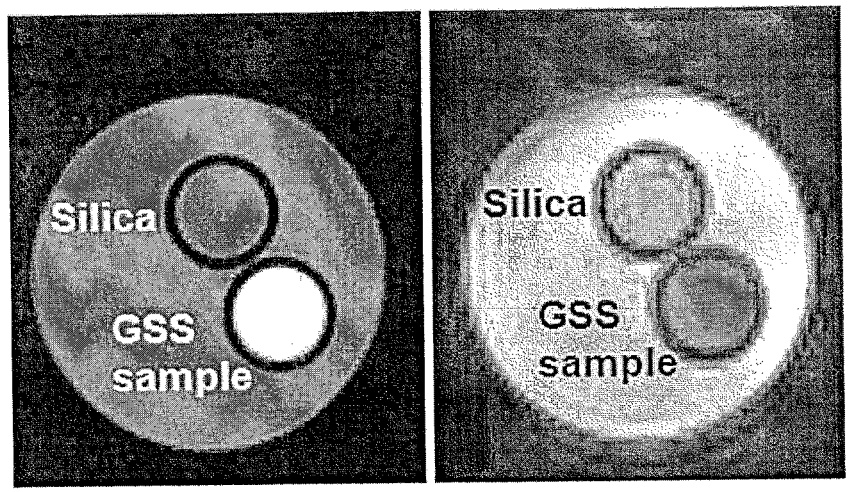
FIG. 4A   FIG. 4B

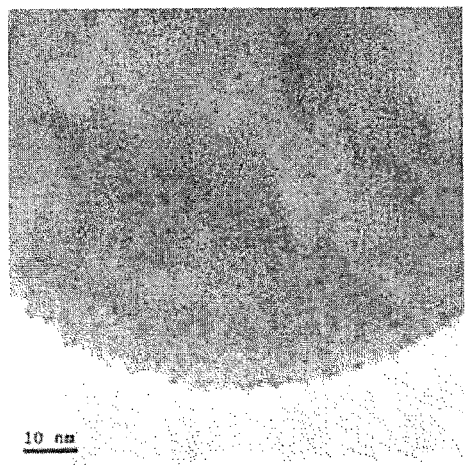 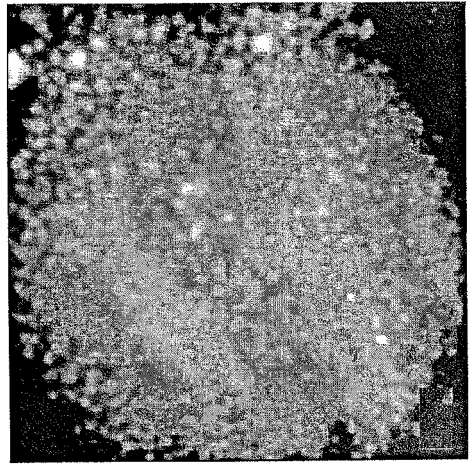
FIG. 7A  FIG. 7B
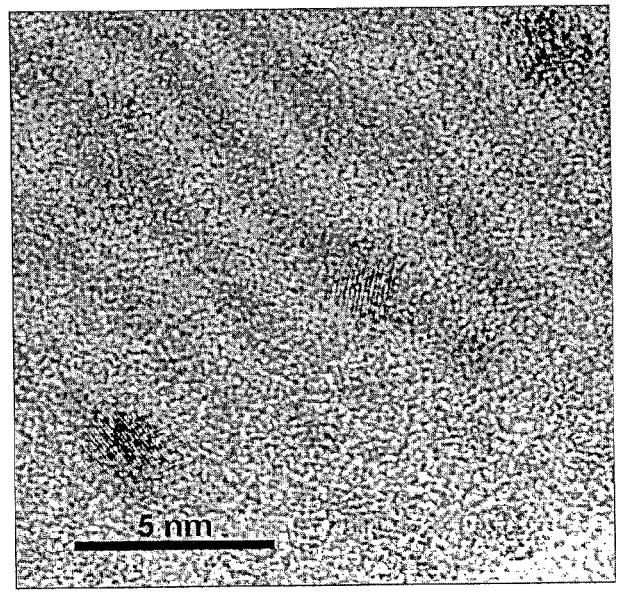
FIG. 8

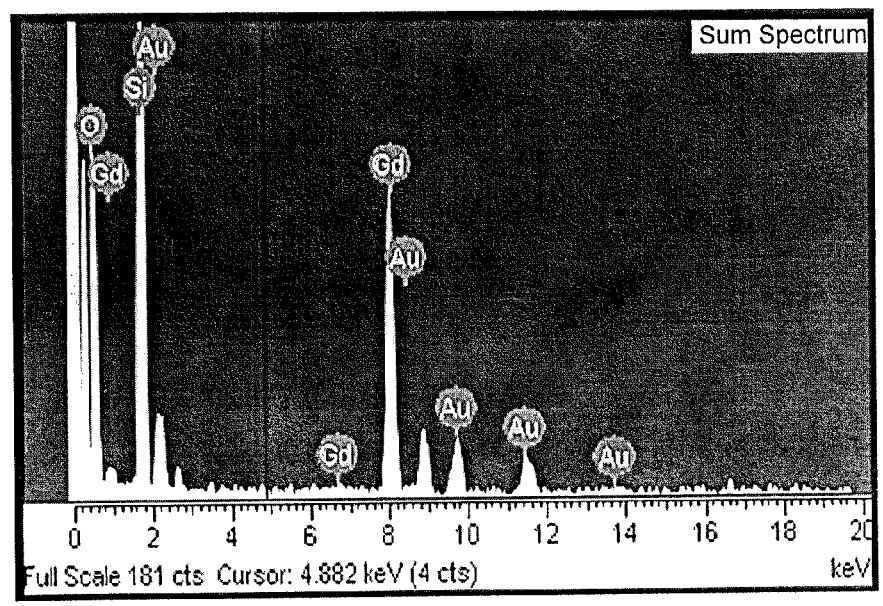
FIG. 9
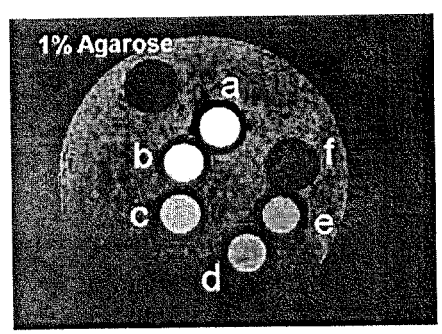 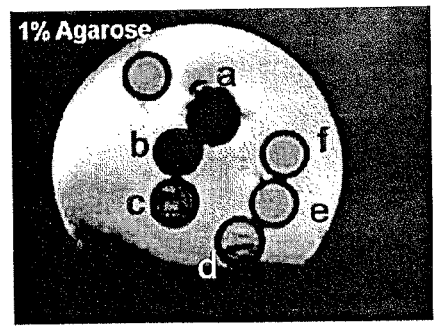
FIG. 10A        FIG. 10B

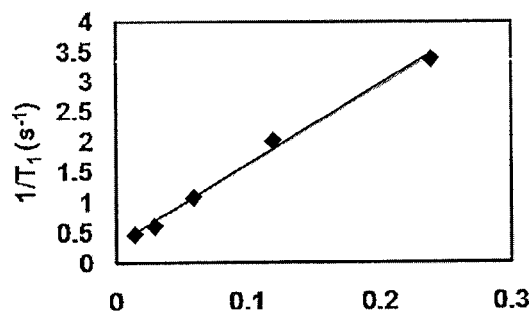 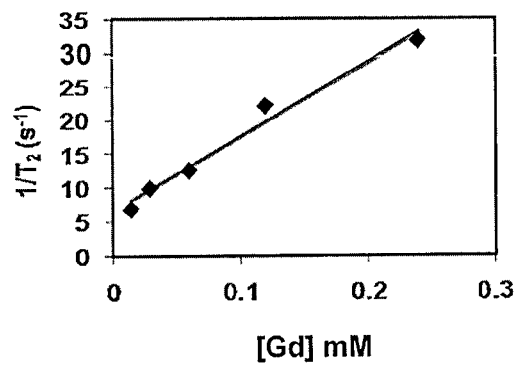
FIG. 11A  FIG. 11B
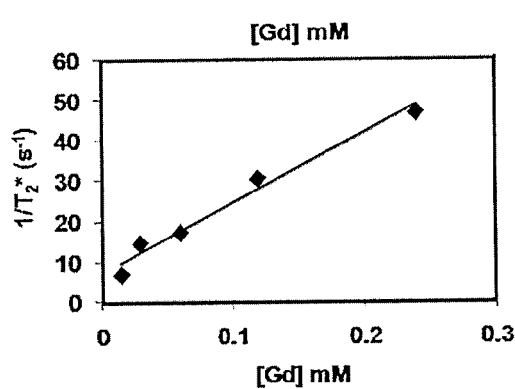
FIG. 11C

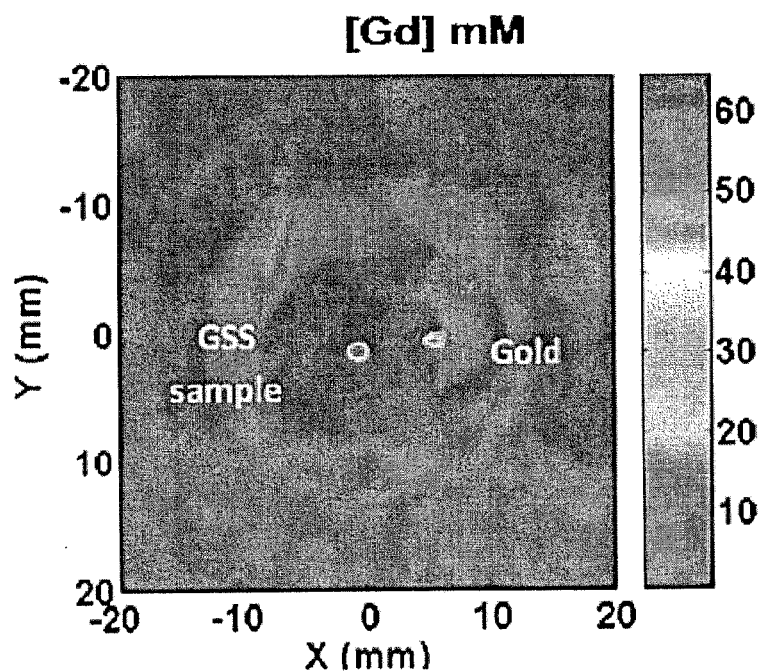
FIG. 12
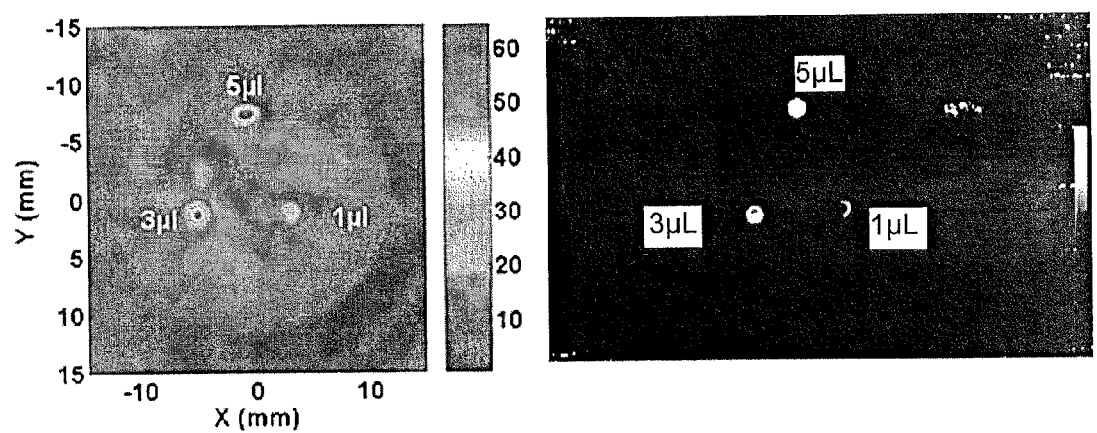
FIG. 13A  FIG. 13B

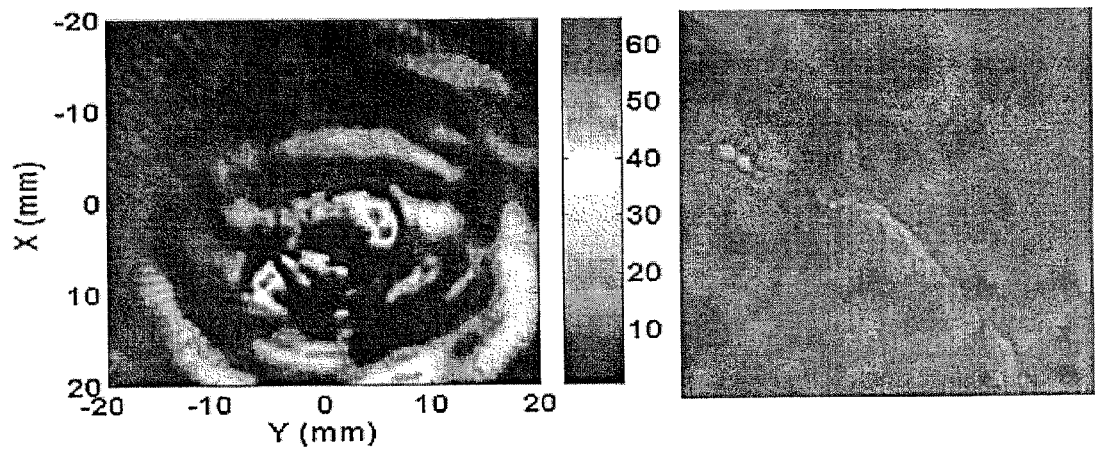
FIG. 19A  FIG. 19B
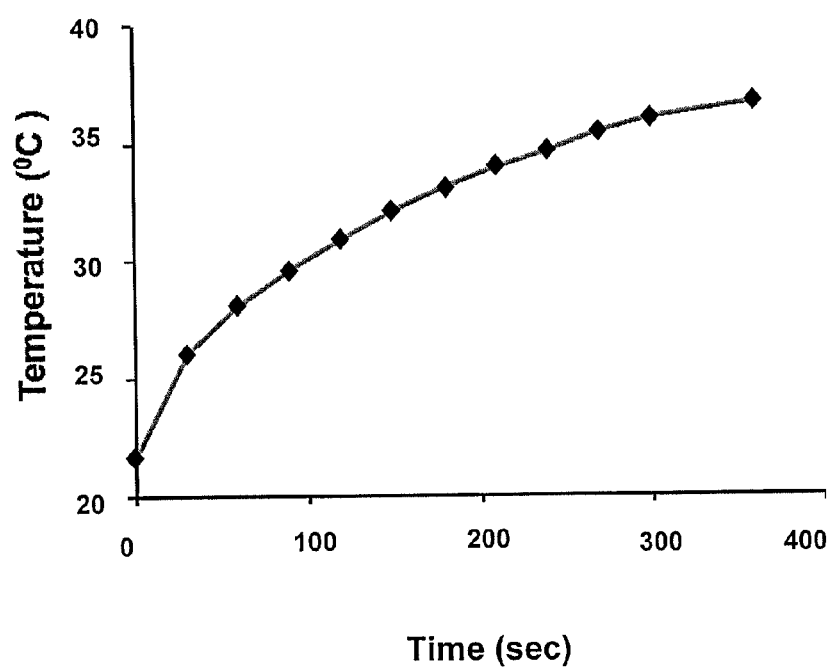
FIG. 20

MULTIMODAL NANOPARTICLES FOR NON-INVASIVE BIO-IMAGING

CROSS REFERENCE TO RELATED APPLICATIONS

The present application is a divisional of U.S. patent application Ser. No. 12/675,633, filed Apr. 14, 2010, which is the U.S. national stage application of International Patent Application No. PCT/US2008/074630, filed Aug. 28, 2008, which claims the benefit of U.S. Provisional Patent Application No. 60/968,476, filed Aug. 28, 2007, the disclosures of which are hereby incorporated by reference in their entireties, including all figures, tables or drawings.

This invention was made with government support under EEC0506560 awarded by the National Science Foundation. The government has certain rights in the invention.

BACKGROUND OF THE INVENTION

Bio-imaging techniques can non-invasively measure biological functions, evaluate cellular and molecular events, and reveal the inner workings of a body. Examples of bio-imaging techniques include magnetic resonance imaging (MRI), positron emission tomography (PET), x-ray tomography, luminescence (optical imaging), and ultrasound. Each of these techniques can differ from one another in the resolution, sensitivity, and anatomical information they provide about the subject. For example, though optical imaging has high sensitivity, it provides limited anatomical background information, and can display artifacts due to tissue absorbance and scattering. Photo acoustic tomography (PAT), an emerging non-invasive imaging modality, uses a non-ionizing optical (pulsed laser) source to generate contrast, which is detected as an acoustic signal whose scattering is 2-3 orders of magnitude weaker than optical scattering in biological tissues, the primary limitation of optical imaging. MRI on the other hand can be used to generate contrast to detect tumors in deep tissue and provide true three-dimensional imaging of biological structures and processes at cellular resolution. X-ray contrast is useful to differentiate tissues with small differences in their opacity.

It is often necessary to use more than one imaging technique to integrate the strengths of each while overcoming the limitations of the individual techniques to improve diagnostics, preclinical research and therapeutic monitoring. However, each of these techniques typically uses a different contrast agent, so using more than one bio-imaging technique requires additional time, expense and can complicate the diagnostic process. It would be desirable to have a multimodal contrast agent that can be used for more than one bio-imaging technique. Multi-modal contrast agents for bioimaging can also serve as important tools for developing and benchmarking experimental imaging technologies by using parallel experiments with mature, proven technologies. The application of multimodal contrast agents is particularly important for developing less expensive, more available, and reliable bio-imaging technologies, such as PAT, that have the potential to make advanced medical diagnostics available to impoverished populations, as well as more commonplace worldwide. Although imaging technologies such as CT and MRI have become prevalent, the related capital costs associated with obtaining and maintaining existing equipment financially limits its widespread application, even in modern societies.

BRIEF SUMMARY OF THE INVENTION

In an embodiments of the invention, a multimodal nanoparticle, for use as a contrast agent for PAT and at least one other imaging method, has a dielectric core of at least one oxide, for example silicon dioxide, with a metal, for example gold, deposited on the dielectric core. The multimodal nanoparticle also has a plurality of at least one moiety that exhibits luminescence, magnetic or paramagnetic properties, x-ray opacity, or any combination of these properties. A single moiety can act as one or more contrast agents for photo acoustic tomography (PAT) imaging, luminescence imaging, magnetic resonance (MR) imaging, and x-ray imaging. The multimodal nanoparticle can have multiple moieties, which behave as different contrast agents for different imaging techniques. For example, in one embodiment a luminescence imaging moiety can be a dye, a quantum dot, a phosphor or a combination thereof. In another embodiment, an MR imaging moiety can be at least one chelated lanthanide or transition metal.

In one embodiment of the invention, the multimodal nanoparticle is a metal speckled particle, for example gold speckled silicate (GSS) nanoparticle. The metal deposition is speckled where a discontinuous metal and dielectric core have a non-discrete interface with an interpenetrated gradient. In an embodiment of the invention, the multimodal nanoparticles can also have a biomolecule or a surface functional group attached to its surface by any means such that the biomolecule or functional group allow specific targeting of a tumor cell.

Another embodiment of the invention is directed to a method for multimodal bio-imaging where a multimodal nanoparticle, as described above, is introduced to a desired location, which is then imaged by photo acoustic tomography (PAT) and at least one other imaging method selected from magnetic resonance, luminescence, and x-rays imaging. The multimodal nanoparticles enhance the contrast observed in the resulting images. The different modes of imaging can be performed simultaneously or sequentially.

Another embodiment of the invention is directed to a method for using multimodal nanoparticles, as described above, for therapeutic purposes where a multimodal nanoparticle is delivered to a desired target region, such as tissue containing tumors. The multimodal nanoparticle can then be irradiated with electromagnetic radiation, which generates heat when the multimodal nanoparticles absorb radiation. Sufficient electromagnetic radiation can be provided to cause local heating that is sufficiently high to kill tumor cells that have the multimodal nanoparticles on or contained within the tumor. Electromagnetic radiation can be from any region of the spectrum including, but not limited to infrared, near infrared, visible, near ultraviolet and ultraviolet. In another embodiment of the invention, irradiation of the multimodal nanoparticles for therapeutic purposes can be neutron irradiation, such that the multimodal nanoparticles emit x-rays, gamma rays or Auger electrons, which destroy cells in the vicinity of the multipurpose nanoparticles.

Another embodiment of the invention is a method for preparing multimodal nanoparticles as described above by forming a core of primarily a dielectric material, depositing a metal on the core, and attaching at least one moiety that exhibits luminescence, magnetic or paramagnetic properties, x-ray opacity, to the core or the metal. The core can be formed by condensation of a metal oxide precursor in a water-in-oil microemulsion. The metal can be deposited by reduction of a dissolved metal salt in the presence of a reducing agent. One moiety that can be attached to the nanoparticle is a chelated lanthanide or transition metal where a ligand bound alkoxysilane chelated to a metal is condensed with the metal oxide precursor during formation of the core or by condensation of the alkoxysilane with a residue from the precursor after formation of the core. Some moieties, such as luminescence providing dyes or phosphors or quantum dots, can be admixing with the metal oxide precursors and be bound or entrapped within the core upon condensation.

BRIEF DESCRIPTION OF THE DRAWINGS

FIG. 3 shows a photo acoustic tomography PAT image of gold speckled silica nanoparticles (GSS) and for a silica particle, according to an embodiment of the invention.

FIG. 4A shows a $T_1$ weighted magnetic resonance (MR) image of a silica particle and that of a Gd-doped GSS sample and FIG. 4B shows a $T_2$ weighted $T_1$ weighted magnetic resonance (MR) image of a silica particle and that of a GSS sample Where The GSS particle imparts a positive enhancement in the $T_1$ weighted image and a negative enhancement for a $T_2$ weighted image, according to an embodiment of the invention.

FIG. 7A shows a high resolution TEM image where dark gold speckles are observed on the silica of a GSS multimodal nanoparticle and FIG. 7B shows a dark field TEM image of the GSS multimodal nanoparticle, according to an embodiment of the invention.

FIG. 8 shows a high-resolution TEM image where the lattice planes of the gold speckles deposited on silica of a GSS multimodal nanoparticle, according to an embodiment of the invention.

FIG. 9 shows an EDS spectrum of Gd-doped GSS multimodal nanoparticles showing the presence of Si, O, Au and Gd, according to an embodiment of the invention.

FIG. 10A shows $T_1$-weighted (repetition time (TR)=11 000 ms, echo time (TE)=4.2 ms), and FIG. 10B shows $T_2^*$ TR=500 ms, TE=40 ms images of serial dilutions of Gd doped GSS nanoparticle (a) 0.24, (b) 0.12, (c) 0.06, (d) 0.03 and (e) 0.015 mM of Gd in 0.5% agarose and (f) 0.5% agarose (as control) according to an embodiment of the invention.

FIGS. 11A-C show linear plots of Gd concentration vs. (FIG. 11A) $1/T_1$, (FIG. 11B) $1/T_2$, and (FIG. 11C) $1/T_2^*$ to determine ionic relaxivities $R_1$, $R_2$, and $R_2^*$ for Gd-doped GSS multimodal nanoparticles according to an embodiment of the invention.

FIG. 12 shows PAT contrast for gold and GSS multimodal nanoparticles of similar size and concentration (8 μL of 10 mg/mL) in a tissue-like phantom with background absorption coefficient μa=0.007 mm$^{-1}$ and reduced scattering coefficient μa'=0.5 mm$^{-1}$ according to an embodiment of the invention.

FIGS. 13A-B show a PAT (FIG. 13A) and MRI $T_1$ (FIG. 13B) contrast from the same phantom using 1, 3 and 5 μL (particle concentration 10 mg/mL) of Gd-doped GSS multimodal nanoparticles with background coefficient μa=0.007 mm$^{-1}$ according to an embodiment of the invention.

FIG. 17A is spin echo (Msme) TR=1 s, TE=30 ms, matrix=256×256, FOV=2.8×2.74 cm, 2 avg, 1 mm slice; FIG. 17B is gradient echo (FLASH) TR=500 ms, TE=4 ms, matrix=256×256, FOV=2.8×2.74 cm, 2 avg, 1 mm slice; FIG. 17C is spin echo (Msme) TR=276 ms, TE=5.5 ms, matrix=128×256, FOV=2.8×2.74 cm, 2 avg, 1 mm slice; and FIG. 17D is spin echo (Msme) fat suppression, TR=276 ms, TE=5.5 ms, matrix=128×256, FOV=2.8×2.74 cm, 2 avg, 1 mm slice, according to an embodiment of the invention.

FIGS. 19A-B show a PAT image (FIG. 19A) of an animal model of a tumor region 3 hours post injection with multimodal nanoparticles after subtracting the initial image, and an ex vivo fluorescence image (FIG. 19B) of the tumor section according to an embodiment of the invention.

FIG. 20 is a plot of temperature rise in a solution containing 10 mg/mL GSS multimodal nanoparticles on exposure to continuous illumination from a 785 nm laser with a 350 mA output, according to an embodiment of the invention.

DETAILED DESCRIPTION OF THE INVENTION

Figure 1:
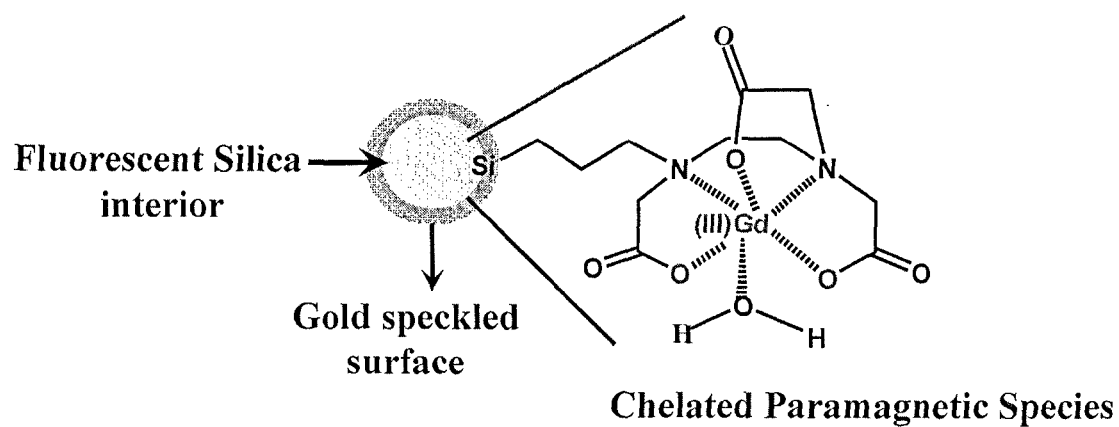
FIG. 1 schematically depicts a multimodal nanoparticle, according to an embodiment of the invention.

According to various embodiments, multimodal nanoparticles have a plurality of agents chosen from fluorescent contrasting agents, MRI contrasting agents, an x-ray contrasting agents, and PAT contrasting agents. A single moiety can function as one on a plurality of contrast agents. Examples of contrast agents for luminescence (such as fluorescence, phosphorescence, and colorimetric) imaging include, but are not limited to, dyes, quantum dots, and phosphors. Examples of MRI imaging contrast agents include, but are not limited to, paramagnetic substances or substances containing particles exhibiting ferromagnetic, ferromagnetic or super paramagnetic behavior. Paramagnetic MRI contrast agents can be, for example, transition metal chelates and lanthanide chelates like Mn-EDTA (ethylene diamine tetraacetic acid) and Gd-DTPA (diethylene triamine pentaacetic acid).

IR absorbing dyes include indocyanine green, Cy-5 and others. Contrast agents for PAT work by selectively absorbing radiation in certain organs, or parts of organs, and efficiently converting that radiation into pressure waves or by scattering and diffusing incipient light so that it more uniformly illuminates the target organs. The radiation may be electromagnetic radiation in the visible, infrared, microwave or other parts of the electromagnetic spectrum. Contrast agents for PAT include, but are not limited to, dyes, metal nanoparticles, metal nanoshells, and metal speckled nanoparticles. Nanoshells can be composed of a dielectric core, usually silica, surrounded by a discrete thin continuous metal shell, typically gold. Metal speckled nanoparticles can be composed of a dielectric core, usually silica, surrounded by an interpenetrated, molecularly seeded, discontinuous gold film. Metal speckled nanoparticles have a non-discrete interface with the dielectric core establishing an interpenetrated gradient between the core and the outer discontinuous metallic film. These features result in alternative physical parameters that can be adjusted and modified to optimize particle performance for imaging and therapeutic applications.

In one embodiment of the invention, multimodal nanoparticle can include a core formed of a dielectric material such as $SiO_2$. The core can include fluorescent dyes, which can cover a desired spectrum range from visible to near IR. In other embodiments of the invention, the core can contain quantum dots and/or phosphors.

In one of the embodiments, multimodal nanoparticle can be doped with a (para) magnetic element, such as lanthanides, including Gd, Eu, Dy, and Tb, and/or transition metals including Mn, Fe etc. These paramagnetic species, in addition to their magnetic influence and ability to generate contrast for MRI, can have a luminescence property. In certain embodiments, these lanthanides function as fluorescent agent in the multimodal nanoparticle in addition to their function as the MRI contrast agent. The heavy atomic weight lanthanides and/or transition elements can function as an X-ray contrast agent in the multimodal nanoparticles.

In one embodiment of the invention, the multimodal nanoparticle contain fluorescent species included on a silica core a paramagnetic element tethered to the particle and speckled with a metallic element, such as gold, silver, copper, or zinc. This interpenetrated, discontinuous metallic surface on the primarily dielectric core imparts photo acoustic contrast from the particle. The metallic element and a lanthanide/transition paramagnetic element provide enhancement to the x-ray contrast. In one embodiment of the invention schematically depicted in FIG. 1, the metallic coating results in a speckled gold nanoparticle, with Gd paramagnetic species and Fluorescein isothiocyanate FITC dye within the silica core. One of ordinary skill in the art will understand that FIG. 1 is exemplary and that other contrast agents, geometries and coatings can be included.

In embodiments of the invention, the nanoparticles can be from less than 50 nm to more than 350 nm in cross section. In one embodiment of the invention, the nanoparticles can be from less than 50 nanometers to about 100 nm in cross section. Generally, but not necessarily, the nanoparticles will be approximately spherical in shape; however, the shape can be that of any ovoid, rod, plate or irregular.

Figure 2:
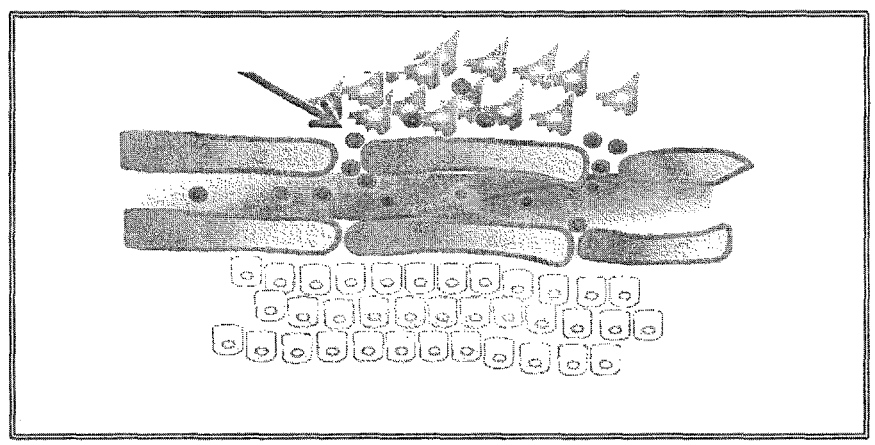
FIG. 2 shows a schematic of passive targeting of tumor cells by multimodal nanoparticles promoted by enhanced permeability and retention, according to an embodiment of the invention.

In addition to the multimodal nanoparticles value as multifunctional contrast agents, in embodiments of the invention, the multimodal nanoparticles can be employed in therapeutic application as traceable hyperthermia agents. The multimodal nanoparticles can be injected into an animal and actively/passively targeted to a tumor site, exploiting the well known enhanced permeability and retention (EPR) effect, as illustrated in FIG. 2. The GSS nanoparticles can absorb light in the visible to Near Infrared (NIR) wavelength range where heat is generated as a result of their absorption. The heat generating ability makes them useful for therapeutic hyperthermia applications. The located tumors can be specifically targeted to heat and destroy the malignant cells that include the multimodal nanoparticles.

Materials And Methods

Materials Tetraethylorthosilicate (TEOS), Triton X-100 (TX-100), n-hexanol, 3-(aminopropyl)triethoxysilane (APTS), and cyclohexane were purchased from Aldrich Chemical Co. Inc. N-(Tri-methoxysilyl-propyl)ethyldiaminetriacetic acid disodium salt (TSPETE) (45% wt % solution in water) was purchased from Gelest Co., gold chloride, gadolinium acetate, and hydrazine hydrate were obtained from Acros Organics, and ammonium hydroxide ($NH_4OH$, 28-30 wt %) was obtained from the Fisher Scientific Co. All other chemicals were of analytical reagent grade. Deionized (DI) water (NANOpure, Barnstead) was used for the preparation of all solutions.

Synthesis of Gd-Doped GSS Nanoparticles. The complete synthesis of the multimodal nanoparticles was done in one pot using reverse micelles. The water-in-oil (W/O) microemulsion was prepared by mixing TX-100 cyclohexane, n-hexanol (1: 4.2:1 v/v), and appropriate water. n-Hexanol was used as a co-surfactant to the nonionic surfactant, TX-100. An amount of 0.050 mL of TEOS was added to the microemulsion and allowed to equilibrate for 30 min. The hydrolysis and polymerization of TEOS was initiated by adding 0.05-0.200 L of $NH_4OH$. The overall $W_0$ (water to surfactant molar ratio) of $NH_4OH$ was 10 after addition. The silica polymerization reaction ran for 24 hour, the surface of the silica nanoparticle was modified with the addition of 0.025 mL of TSPETE and 0.050 mL of TEOS. The resulting solution was stirred overnight. Subsequently, 0.10 mL of 0.1 M Gd(III) acetate solution was added and stirring for 4 hours. This was followed by addition of 0.5 mL of 0.25 M $HAuCl_4$, prepared in degassed water, and 1.1 M solution of reducing agent (hydrazine hydrate). The solution was stirred for about 12 hours. The progress of the reaction at each step was monitored by UV-vis absorption spectroscopy. The Gd-doped GSS nanoparticles were isolated from the microemulsion by adding 5 mL of 200 proof ethanol. The solution was stirred for a few minutes. This led to the complete breakdown of reverse micelles with the formation of two immiscible layers of aqueous ethanol and cyclohexane. The nanoparticles along with the surfactant molecules were accumulated in bottom ethanol layer. The top layer of cyclohexane was carefully removed, and the particles were centrifuged. The particles were washed three times with ethanol and five times with water in order to remove surfactant molecules completely. Each centrifugation step, during washing was followed by vortexing and sonication to redisperse the pelleted particles. After complete removal of surfactant, the particles were redispersed in Nanopure water to obtain a concentration of about 2 mg/mL for further characterization.

Particle Size Measurements. The particle size and distribution were measured by dynamic light scattering (DLS) using a Microtrac NANOTRAC and CPS disk centrifuge. The size and morphology of the particles were determined by transmission electron microscopy (TEM). TEM and energy-dispersive X-ray spectroscopy (EDS) spectra of the particles were done using JEOL 2010F transmission electron microscope.

Inductively Coupled Plasma Experiments. Inductively coupled plasma (ICP) measurements were performed using a Perkin-Elmer Plasma 3200 system equipped with two monochromators covering the spectral range of 165-785 nm with a grated ruling of 3600 lines/mm. Briefly, 0.050 g of the nanoparticle sample was digested using aqua regia solution. [Caution: Aqua regia digestion should be performed with care in a hood. Its reaction with GSS nanoparticles produces acrid and toxic fumes.] Au and Gd completely dissolved in the aqua regia, whereas the silica matrix settled at the bottom of the container as a white powder. After complete digestion, the solution was filtered to separate the silica particles as residue. The particles were washed three times with aqua regia solution and twice with nanopure water. The filtrate and the particles were all collected together and boiled to concentrate the volume to 15.0 mL. After instrument calibration was performed for Au and Gd estimation, the filtrate was analyzed by ICP for quantitative estimation of Gd and Au.

MR Phantom Preparation for Relaxometry Measurements. MRI measurements were recorded using a 4.7 T Bruker Avance MR canner. Particle phantom were prepared for MR relaxometry measurements by serially diluting a 10 mg/mL stock solution of Gd-doped GSS nanoparticles with doubly distilled $H_2O$ and a 1% agarose solution (Ultra-Pure agarose, Invitrogen, Carlsbad, Calif.) yielding a total concentration of 0.5% agarose. The resulting nanoparticle concentrations of 5, 2.5, 1.25, 0.625, and 0.3125 mg/mL were then injected into 100 μL capillary tubes (Curtin-Matheson Scientific, 181 Broomall, Pa.) and allowed to solidify on ice, thereby eliminating sedimentation during relaxometry measurements. The comparison of MR response between Gd-doped GSS nanoparticles and silica nanoparticles (without any gold or Gd) was performed similarly by diluting 10 mg/mL nanoparticles in 1% agarose solution, confirming that the silica matrix alone does not exhibit significant photo acoustic and MR contrast. FIG. 3 and FIG. 4 demonstrate that silica does not exhibit significant photo acoustic or MR contrast respectively. Control phantoms containing just 0.5% 187 and 1% agarose were simultaneously imaged to determine effect of agarose on relaxation times. Right before imaging, all samples were placed together inside a water-filled FACS tube (BD Falcon, Franklin Lakes, N.J.) to avoid susceptibility artifacts from the surrounding air.

MR Relaxoinetry for Gd-Doped GSS Nanoparticles. All relaxometry data was acquired at a 4.7 T horizontal bore magnet with Paravision software (PV3.02; Bruker Medical). For measuring $T_1$ relaxation times, axial spin-echo (SE) scan sequences were obtained with TE=4.5 ms, matrix size) 128× 128, FOV=2.8 197×2.8 cm$^2$, spectral width=180 kHz, one average, 1 mm slice thickness, and varying TR values of 11, 6, 3, 1.5, 0.75, 0.5, 0.25, 0.125, 0.075, 0.05, 0.025, and 0.015 s. For $T_2$ relaxation measurements, axial $T_2$-weighted single-slice multiecho images were obtained with TR=11 s, TE=5 ms, ΔTE=5 ms (60 echoes), matrix size=128×128, FOV=2.8×2.8 cm$^2$, spectral width=100 kHz, two signal averages, and1mm slice thickness. Analysis of $T_1$ and $T_2$ values was performed using Paravision 3.02 software where $T_1$ and $T_2$ maps were calculated assuming a monoexponential signal decay and by using a nonlinear function, least-squares curve fitting on the relationship between changes in mean signal intensity within a region of interest (ROI) to TR and TE. $T_1$ and $T_2$ relaxation times(s) for the Gd-doped GSS nanoparticles in 0.5% agarose were then derived by ROI measurements of the test samples converted into $R_1$ and $R_2$ relaxation rates ($1/T_{1,2}$ (s$^{-1}$). Finally, $R_{1,2}$ values were plotted against the concentration of Gd on the nanoparticle and $r_1$ and $r_2$ (mM$^{-1}$s$^{-1}$) relaxivities were obtained as the slope of the resulting linear plot.

$T_2$* relaxometry measurements were acquired by $T_2$*-weighted FLASH gradient echo scan sequences. TRs were kept constant at 500 ms with varying TEs of 4, 8, 12, 16, 20, 40, 60, and 100 ms, FOV=2.8×2.8 cm$^2$, matrix size=256× 256, two signal 219 averages, spectral width=60 kHz, and 1 mm slice thickness. Image J software (NIH) with an MR analysis calculator plug-in was used to quantify $T_2$* values by stacking the individual FLASH sequences with varying TEs and creating a $T_2$* map. ROIs for each cell sample were then drawn to contain the entire cross section of each of the samples, and values were then plotted as $R_2$* (or the inverse of $T_2$* ($1/T_2$*, (s$^{-1}$))), against the concentration of Gd in the sample (Excel, Microsoft Inc.). $R_2$* relaxivity (mM$^{-1}$s) was later obtained as the slope of the resulting linear plot. Data are presented as the mean±SD of measurements.

PAT Instrumentation. A mechanical scanning photoacoustic system with single acoustic transducer to collect the acoustic signals was utilized. A pulsed Nd:YAG laser (Altos, Bozeman, Mont.) working at 532 nm with 4 ns pulse duration, 10 Hz repetition rate and 360 mJ maximum pulse power acted as light source. The diameter of laser beam was expanded to 30 mm by a lens. An immersion acoustic transducer with 1 MHz nominal frequency (Valpey Fisher, Hopkinton, Mass.) was driven by a motorized rotator to receive acoustic signals and 360° for phantom cases at an interval of 3°, and thus 120 measurements were performed for one planar scanning, respectively. The scanning plane could be adjusted along the z-axis by mounting the rotator and the transducer on a platform driven by a linear stage. The acoustic transducer was immersed into the water tank while the phantom was placed at the center of the tank where it was illuminated by the laser. The complex wave field signal was amplified by a pulser/receiver (GE Panametrics, Waltham, Mass.) and then was acquired by a high-speed PCI data acquisition board. PAT images were reconstructed by a reconstruction algorithm that is based on the finite element solution to the photoacoustic wave equation in the frequency domain, which can provide stable inverse solutions. Phantoms for imaging were constructed using intralipid, India ink, distilled water, and 2% agar powder as described above. The diameters of all phantoms used in this study were 25 mm. The absorption and reduced scattering coefficients (optical properties) of these phantoms were 0.007 and 0.5 255 mm$^{-1}$, respectively. Nanoparticles were embedded in the phantom 256 at a depth of 2 mm for imaging.

Macrophage Labeling and Phantom Preparation for MRI and PAT. Mouse monocyte/macrophage J774 cells were defrosted, resuspended in DMEM complete, consisting of Dulbecco's modified agle's medium (DMEM) (GIBCO, Grand Island, N.Y.) supplemented with 10% fetal bovine serum (Summit Biotechnology, Ft. Collins, Colo.), 1% glutamax (GIBCO), 1% penicillin/streptomycin (GIBCO), and incubated at a density of 5×10$^5$ cells/mL in 100 mm culture dishes at 37° C. and 5% CO2. Media was replaced 24 h after plating, and the cells were allowed to attach and grow to confluency (usually within 2-3 days). Old media was replaced with fresh before the cells were harvested and washed twice by spinning them down at 1100 rpm for 5 min using a Sorvall RT7 plus ultracentrifuge and resuspending in fresh DMEM complete media. Cells were subsequently replated at a density of 2×10$^5$ and again allowed to attach and grow to confluency. Cells were passaged for 3-4 times before the start of the labeling experiment. During labeling, $1\times10^6$ freshly split J774 cells/mL DMEM complete were incubated overnight with 100 μg/mL of Gd-doped GSS nanoparticles in a six-well tissue culture dish. The next day label-containing media was aspirated off and replaced by fresh media before labeled and unlabeled control cells were scraped up, washed twice in ice-cold Dulbecco's phosphate-buffered saline (DPBS) (GIBCO, Grand Island, N.Y.), counted, and resuspended at a density of $3.33\times10^7$ cells/mL each in DPBS ($2\times10^6$ cells in 60 μL DPBS). Cells were kept on ice until the time of imaging when 20 μL of cell suspension was then injected in the phantom. The same phantom was used for MRI and PAT experiments in succession.

MRI Measurements on J774 Cells Labeled with Gd-Doped GSS Nanoparticles. The sample phantom containing GSS-labeled J774 and control cells was placed inside a solenoid coil and imaged at 4.7 T magnetic field strength with Paravision software (PV3.02; 288 Bruker Medical). $T_1$- and $T_2$-weighted SE scan sequences were used to detect Gd on the nanoparticles inside the cells. For generating $T_1$-weighted images a multislice multiecho (MSME) pulse sequence was used with TR=500 ms, TE=5 ms, matrix size=256×256, FOV=3×3 cm$^2$, spectral width=100 kHz, two signal averages, and a1mm slice thickness. $T_2$-weighted images were acquired either by using a MSME pulse sequence with TR=500 ms, TE=100 ms, matrix size 256×256, FOV=3×3 cm$^2$, spectral width=100 kHz, two signal averages, and a1mm slice thickness or by using a rapid acquisition with relaxation enhancement (RARE) pulse sequence with TR=1000 ms, TE=12 ms, matrix size=256×256, FOV=3×3 cm$^2$, spectral width=60 kHz, four signal averages, RARE factor=8, and a1mm slice thickness.

In one embodiments of the invention, gold-silica hybrid material termed gold speckled silica (GSS) nanoparticles are provided. These MRI-PAT-active multimodal nanoparticles have a surface layer composed of discontinuous, irregular gold nanodomains of varying crystallinity that are incorporated within the pores and on the exterior of the supporting silica matrix. The multitude of dielectric-metal interfaces created by this method gives rise to unique photothermal properties that enable the use of these materials as contrast agents in PAT. The multimodal GSS nanoparticles possess high relaxivity for MRI and at the same time produce a strong PAT contrast.

Figure 5A:
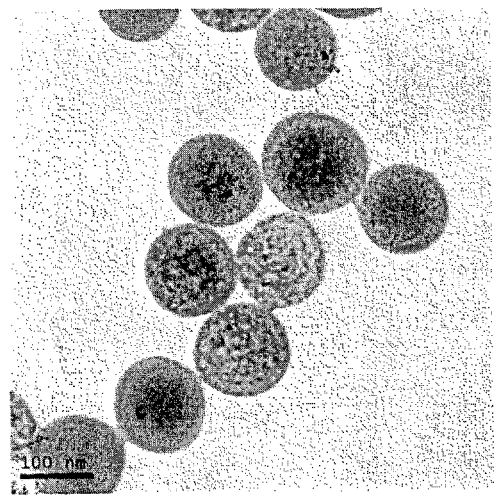
FIGS. 5 A-B show transmission electron microscopic (TEM) images of Gd-doped GSS multimodal nanoparticles of about 100 nm (FIG. 5A) and about 50 nm (FIG. 5B), according to an embodiment of the invention.
Figure 5B:
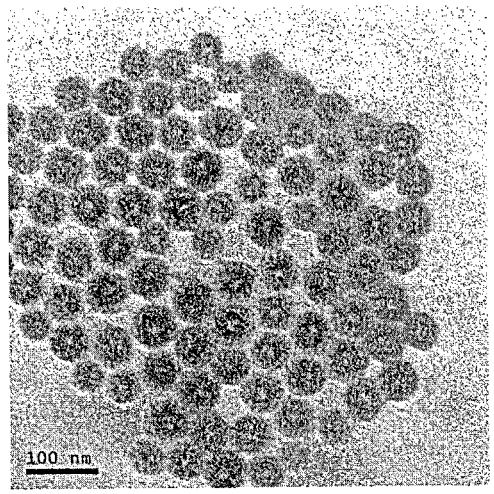
Figure 6:
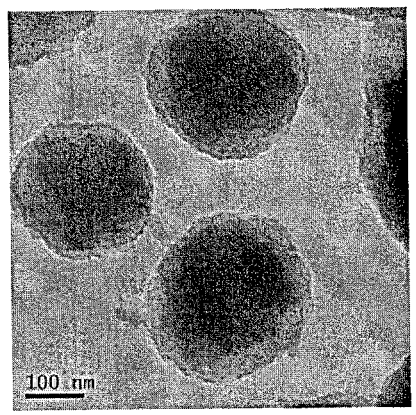
FIG. 6 shows a TEM image of Gd-doped GSS multimodal nanoparticles of about 225 nm, according to an embodiment of the invention.

In one embodiment, the GSS nanoparticles are formed by first forming Gd-doped silica nanoparticles by co-condensation of TEOS and a silane reagent that strongly chelates polyvalent metal ions (TSPETE) in the water core of the TX-100/n-hexanol/water W/O microemulsion. Incorporation of chloroauric acid followed by its reduction was then carried out within the surface layer of the silica nanoparticles. By manipulating $W_o$ of the microemulsions and the reactant concentrations, we were able to tune Gd-doped GSS nanoparticle size from less than 50 to 200 nm. FIGS. 5(a) and 5(b) show representative TEM micrographs for two different samples prepared at $W_0$ 10 and 14, depicting mean particle size of about 100 (+10) and 55 (±5) nm, respectively. GSS nanoparticles up to 200 nm and larger were synthesized at $W_0$ 5 using the same microemulsion system. FIG. 6 shows large sized (>200 nm) GSS nanoparticles prepared in the Tx-100/cyclohexane/water system at $W_0$=5, following the conditions as described above.

The particle sizes were confirmed using DLS and disk centrifuge techniques. In one embodiment of the invention, by incubating Gd-doped silica nanoparticle within the aqueous core of the microemulsion with chloroauric acid, gold ions permeate further into the mesoporous silica matrix. Upon reduction, a unique gold-speckled surface results due to the deposition of the gold nanodomains. The gold nanodomains are discontinuous, randomly deposited, sometimes templated, and irregular gold nanoclusters can form within and on the surface of the silica core. High-resolution TEM (HR-TEM) micrographs of about 100 nm Gd-doped GSS nanoparticles (prepared at W0=10) demonstrate speckled surface deposits of gold, as seen in areas of darker contrast on the silica surface in FIG. 7(a) and as areas of lighter contrast in the dark-field TEM shown in FIG. 7(b). Note that Gd doping also contributes to the background as a darker and lighter haze in FIG. 7(a) and FIG. 7(b), respectively. The HRTEM micrograph of FIG. 8 shows scattered deposition of gold nanoparticles ranging from less than 1 to 5 nm, with varying crystallinity, on the silica surface. These random and irregular clustered deposits include templated deposits. The mesopores make this class of particles distinct and accounts for their unique optical properties such as efficient photothermal properties. Since these particles were also doped with Gd ions, a paramagnetic species that affects the longitudinal relaxation rate of water, they provided MRI contrast.

The elemental composition of the Gd-doped GSS nanoparticles particles was determined using EDS and ICP techniques. An EDS spectrum is shown in FIG. 9 with spectral counts corresponding to Si, O, Au, Gd, and the overall spectrum for the nanoparticle, respectively. The elemental composition as determined by ICP gave average number of atoms of Au and Gd to be about 426 200 and about 34 000 per nanoparticle, respectively. Theoretical calculations showed that about 72 times more number of gold atoms would be present in a single gold nanoparticle of similar dimension.

Figure 14:
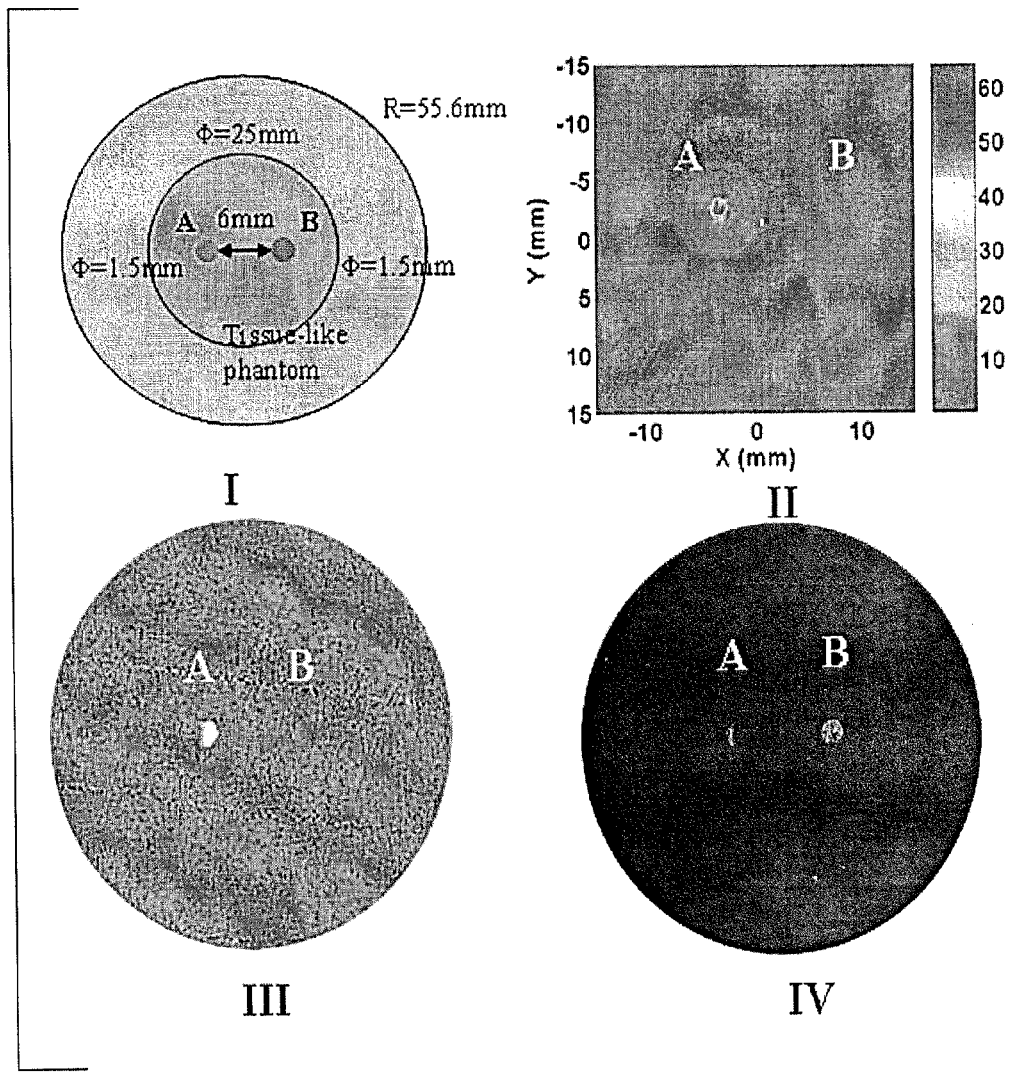
FIG. 14 Panel I shows the position of J 774 microphage cells labeled with GSS multimodal nanoparticles marked as A and unlabeled cells marked as B in a phantom; Panel II shows the PAT image; Panel III is a $T_1$-weighted spin-echo image with TR=500 ms; and Panel IV is the $T_2$ weighted spin-echo image with TR=500 ms, TE=100 ms according to an embodiment of the invention.

The Gd-doped GSS nanoparticles generated MR contrast on both $T_1$ and $T_2$ proton relaxation time weighted sequences, as are shown in FIG. 10(a) and FIG. 10(b). Quantitatively, MR contrast is evaluated by the relaxivity of the nanoparticle. The relaxivity ($R_i$, i=1, 2) is defined as the gradient of the linear plot of relaxation rates ($1/T_i$, i=1, 2) versus Gd concentration [Gd], i.e., $1/T_i=1/T_o+R_i[Gd]$, where Ti is the relaxation time for a contrast agent solution concentration [Gd] and $T_o$ is the relaxation time in the absence of a contrast agent. From the data shown in FIG. 11, the relaxivities $R_1$, $R_2$, and $R_2$* are determined to be 13, 110, and 173 mM$^{-1}$s$^{-1}$, respectively. Gd-GSS exhibit much higher relaxivity values than commercially available contrast agents under the same magnetic strength of 4.7 T. In MRI, it is well-established that the Gd-generated MR contrast relies on the relaxation process of the water molecules in association with the Gd ion and those exchanged in the surrounding environment. For an efficient relaxation process, rapid water exchange between bound (or inner coordination water) with the bulk water and slow tumbling play an important role. The Gd-doped GSS nanoparticles address both these factors. First, the presence of the discontinuous GSS surface allows sufficient bulk water exchange with the Gd ions enabling MR tracking ability. In comparison, a continuous gold shell over the silica core could limit the extent of water exchange inhibiting $T_1$ contrast. Second, tumbling rates are another important factor for producing an effective MRI contrast is also reduced in the Gd doped GSS particles through the rigid binding of Gd to the nanoparticle surface. Because the tumbling rates are mass dependent, nanoparticles are much slower than free Gd chelates and thus produce an enhanced relaxation. One of the major limitations of current molecular chelates used as MR contrast agent is their low sensitivity; this requires the use of higher dosages and results in poor targetability. Both of these problems are addressed by embodiments of the invention. Approximately, 34 000 ions of Gd are captured per nanoparticle with an average size of 100 nm, which is higher than the number of Gd ions previously reported in other nanoparticles such as synthetic polymers (6-70 ions) and in dendrimers (between 5 and 1331 ions, strongly dependent on particle size) and comparable to perfluorocarbon nanoparticles (90 000 Gd ions in 250 nm diameter particle). The ability of Gd-GSS nanoparticles to generate photoacoustic contrast was confirmed by placing the particles in an agar phantom containing India ink and intralipid to simulate tissue-like absorption and scattering. FIG. 12 shows the comparison of PAT contrast from GSS nanoparticles and compares it to that of similar size and concentration of gold nanoparticles. The dark red region in the area of the nanoparticles, with respect to the blue background, demonstrates that a strong PAT contrast is observed from the particles. As shown in FIG. 12, the GSS nanoparticles generated a stronger photoacoustic signal when compared the GSS nanoparticles, in spite of the presence of ~72-fold less gold atoms, demonstrates them as a better PAT contrast agent. Control experiments were also performed using silica nanoparticles (without Au or Gd) which illustrated that the bare silica nanoparticles do not have a significant PAT contrast. Because the PAT originates from the optical absorption of the illuminating laser wavelength, the GSS particles also hold therapeutic potential for the thermal ablation of tumors. Hence, the particles described here hold both multimodal imaging as well as therapeutic capabilities. To evaluate the bimodal character of the GSS nanoparticles, simultaneous MR and photoacoustic evaluation was carried out. To achieve this, the GSS particles were placed in tissue-like phantom. The phantom was imaged for PAT and MR in succession, and the results are shown in FIGS. 13(a) and (b), respectively. An increase in the MR and PAT signal intensity is observed with increasing particulate concentration. In vitro studies were carried out with the GSS nanoparticles to assess the functional ability of the particles in the cellular environment. The uptake of the GSS nanoparticles by J774 macrophages was carried out as described above. The cells were placed in tissue-like phantom and imaged by PAT and MRI in succession. FIG. 14 shows the phantom design with the sample placement and the MR and PAT images obtained with the same phantom. It is observed that the cells labeled with the GSS nanoparticles produce a strong PAT contrast as compared to the background. The MRI image of the same phantom shows the ability to generate the $T_1$ and $T_2$ contrast. The in vitro experiments demonstrated the capability of the GSS nanoparticles to generate an efficient PAT and MR contrast in contrast in living cells, showing potential use of GSS nanoparticles as in vivo cell tracker.

Figure 15A:
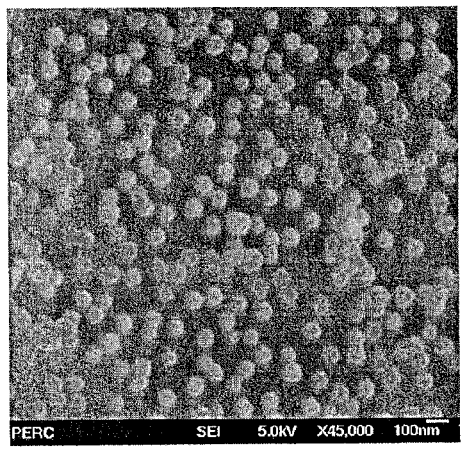
FIGS. 15A-B show representative (FIG. 15A) SEM and (FIG. 15B) TEM images of multimodal nanoparticles according to the invention.
Figure 15B:
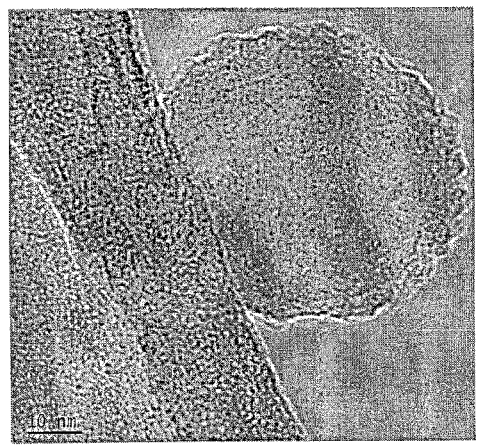

Multimodal nanoparticles with silica core according to an embodiment of the invention can be made fluorescent by coupling Fluorescein isothiocyanate (FITC) can be prepared in the manner described above for the GSS particles. A lanthanide metal was attached to the surface of the core by co-condensing a silane ligand on the silica surface. The particle surface was then coated with gold within the water core of the microemulsion. This led to the gold speckled surface coated multimodal nanoparticles shown in FIGS. 15(a) and 15(b) as SEM and TEM images, respectively, of the multimodal nanoparticles. Using Dynamic Light Scattering, the size of the multimodal nanoparticles was determined to be about 50 nm to about 100 nm.

The multimodal nanoparticles generated contrast in MR images, where glass micropipettes (250 μL in volume) were filled with about 200 μL of serial dilutions of multimodal particles and placed in a single-tuned solenoid coil (200 MHz) with an inner diameter of 1 cm, and data were recorded at room temperature using a 4.7 T (200 MHz) Bruker Avance MR scanner. $T_1$, $T_2$, and $T_2^*$ relaxivities for the particles were determined from the slope of the relaxation graphs obtained by serial dilutions of the sample normalized to Gd. The $T_1$ contrast generated from the serial dilutions of the nanoparticles at 5 mg/mL, 2.5 mg/mL, 1.25 mg/mL, 0.625 mg/mL, 0.3125 mg/mL suspended in 0.5% agarose with a $T_R$ of 11000 ms and $T_E$ of 4.5 ms was clearly enhanced relative to 1% and 0.5% agarose solution controls.

PAT contrast from the multimodal nanoparticles was determined where pulsed light with incident fluence of 10 mJ/cm$^2$, well below the safety standard from a Nd:YAG laser (wavelength: 532 nm, pulse duration: 4 ns) was coupled into the phantom via an optical subsystem and generated acoustic pressure wave. A wide-bandwidth, 1 MHz transducer was used to receive the acoustic signals. The transducer and the phantom were immersed in a water tank. A rotary stage rotated the receiver relative to the center of the tank. One set of data was taken at 120 positions when the receiver was scanned circularly over 360°. The PAT picture was generated by processing the data collected using standard algorithms.

Figure 16:
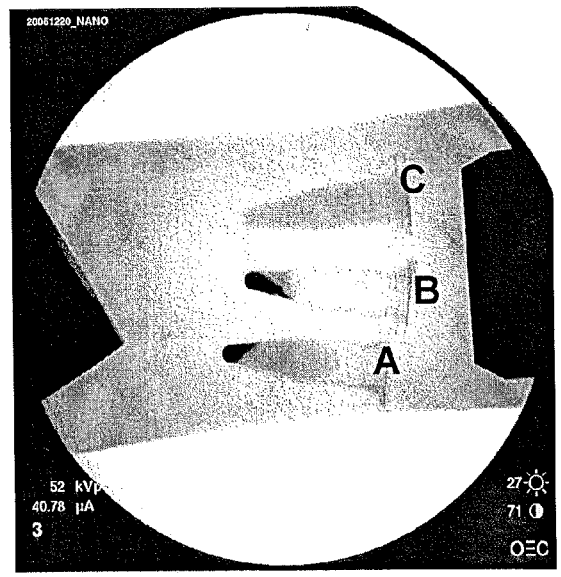
FIG. 16 shows x-ray contrast from the multimodal nanoparticles (A and B) showing strong contrast to that of water (C) according to an embodiment of the invention.
Figure 17A:
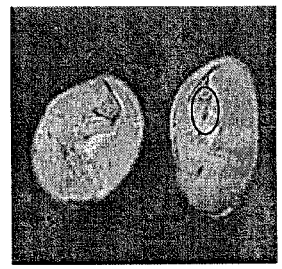
FIGS. 17A-D show in-vivo MR images of multimodal nanoparticle labeled J74 cells in mouse leg where.
Figure 17B:
Figure 17C:
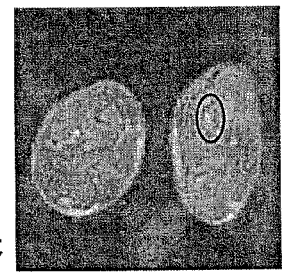
Figure 17D:
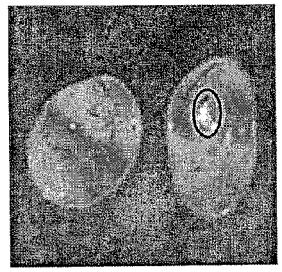

The ability to generate x-ray contrast by the multimodal particles was demonstrated by suspending about 20 mg/ml of nanoparticles in nanopure water, using nanopure water as control. FIG. 16 shows the strong x-ray contrast generated from the iron doped multimodal nanoparticles.

In vivo testing using the exemplary multimodal nanoparticles for MRI and PAT was then performed. Two (2) million J77 4 cells labeled with the multimodal nanoparticles were injected into the right leg of the mouse while unlabeled cells were injected into the left leg. The animal was MR imaged on 4.7 T MRI scanner immediately following injection. The in vivo MR images shown in FIG. 17 demonstrate the ability of the particles to generate sufficient MR contrast in live animals.

Figure 18:
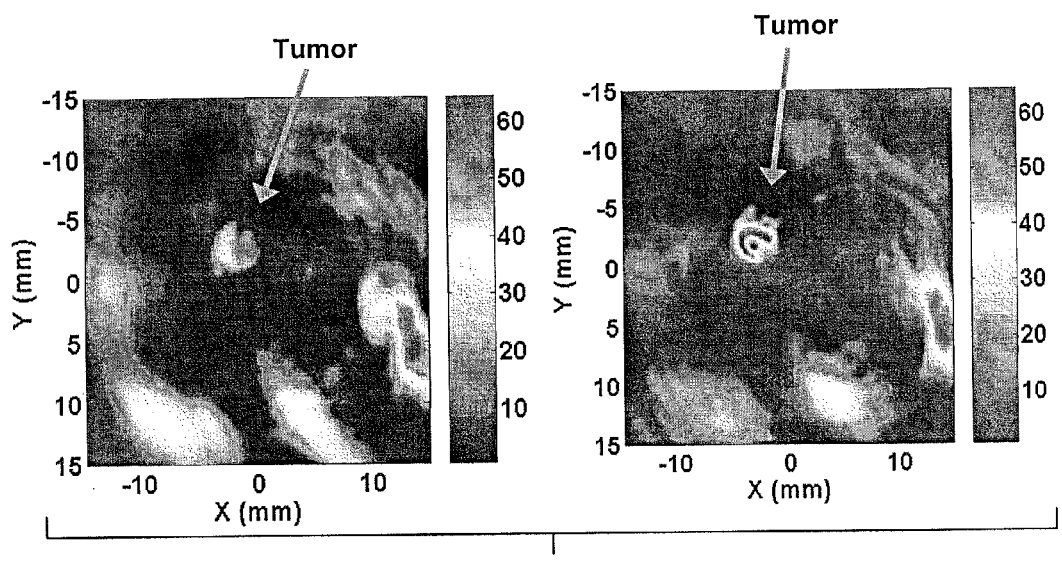
FIG. 18 shows PAT images of a mouse before (left) and after (right) the injection with the multimodal nanoparticles where the red (appearing as a plurality of dark regions within a white region of the image) shows the contrast in the presence of the multimodal nanoparticles according to an embodiment of the invention.
Figure 21A:
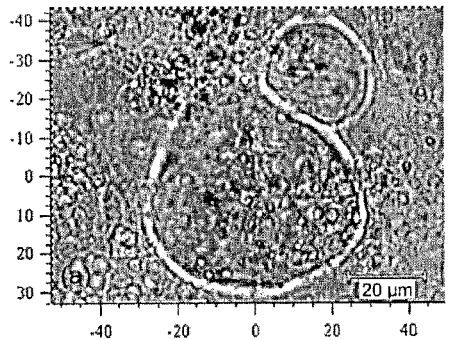
FIGS. 21A-D show an A549 cell with GSS multimodal nanoparticles before laser exposure (FIG. 21A) and after laser exposure (FIG. 21B) for 100 s, which formed a bubble due to the heating and an A549 cell before laser exposure (FIG. 21C) and after laser exposure (FIG. 21D) for 100 s without bubble formation according to an embodiment of the invention.
Figure 21B:
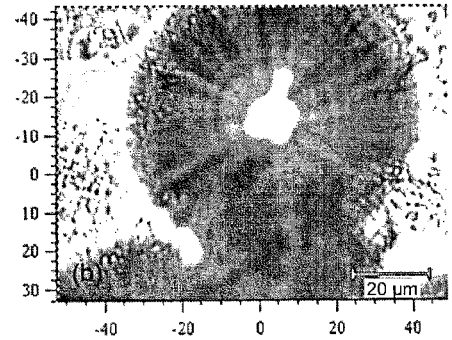
Figure 21C:
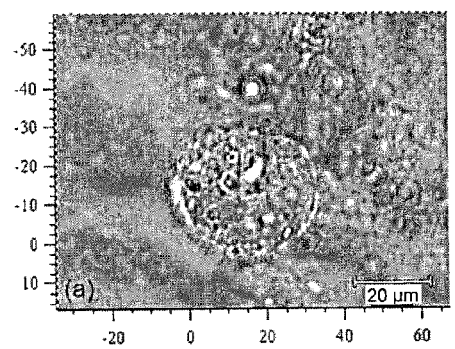
Figure 21D:
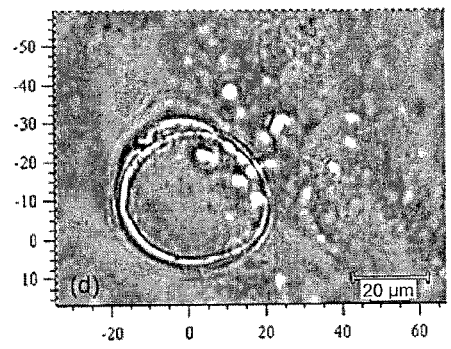

An MCF7 tumor was grown in the mouse abdomen. PAT images were taken before and after the injection of multimodal nanoparticles injected in the MCF7 tumor. FIG. 18(a) and FIG. 18(b) show the PAT images obtained under similar experimental conditions for a tumor before and after injection with the multimodal nanoparticles. It is shown clearly that the particles can be used to image the tumor, in vivo conditions.

GSS nanoparticles doped with FITC dye were prepared in the microemulsion in the above described manner. GSS nanoparticles were pegylated by reacting with Peg-thiol using standard protocols. 100 ul (particle concentration 10 mg/mL) pegylated nanoparticles were injected in the tail vein of the animal model (breast cancer). The tumor region in the animal was monitored by PAT before and after the injection of nanoparticles at 1, 3 and 5 hour interval. The nanoparticles injected into the animal model were passively targeted to the tumor site by the well known Enhanced permeability and retention (EPR) effect.

Results from a PAT experiment and ex-vivo fluorescence studies are shown in FIG. 19. FIG. 19(a) shows a representative PAT image from subtraction of initial PAT image (prior to injection of nanoparticles) from the PAT image obtained 3 hour post injection. The deep red regions (appearing as a plurality of dark regions within a white region of the image) result from the localization of the GSS particles around the tumor. To confirm the findings from PAT imaging, tumor sections from the animal model were checked for fluorescence after sacrificing the animal. FIG. 19(b) shows the fluorescence image of the tumor tissue section. The green fluorescence (white in the grayscale reproduction of the image) emanates from the presence of fluorescent—GSS nanoparticles (FITC) in the tumor vasculature and the blue fluorescence (gray in the grayscale reproduction of the image) is seen from the nuclear stain DAPI. Hence, this confirms that GSS nanoparticles can be tracked non-invasively using PAT in vivo and their position can be confirmed by a second mode (fluorescent) in the multimodal nanoparticles. The GSS nanoparticles have an absorption maximum at about 530 nm and, in general, strongly absorbs in the region of 450 to 850 nm. This absorption is remarkably different from the starting materials i.e. silica and gold chloride. The light absorbing character of GSS nanoparticles in the visible to Near Infrared (NIR) wavelength range makes the particles generate heat as a result of such absorption making them useful for therapeutic hyperthermia applications. FIG. 20 shows the rise in temperature of solution containing GSS nanoparticles (10 mg/mL) when illuminated with 785 nm NIR laser. The laser output was maintained at 350 mA during the experiment. GSS nanoparticles showed a rise of ~15° C. in 5 minutes on continuous illumination with NIR laser as compared to about 1° C. rise observed with nanopure water. For hyperthermia, an increase of about 8-10° C. over the normal physiological temperature is known to cause disruption of the cellular metabolism leading to eventual death. From the above results it is apparent that GSS nanoparticles are capable of sufficiently elevating the temperature to kill tumor cells.

Lung A549 cancer cells were dosed with GSS nanoparticles in various combinations of time and concentration; 18 hrs incubation for 5 and 10 μg/ml; and 24 hrs incubation for 20 μg/ml. Prior to illuminating the cells with a 785 nm laser, the media was removed and the cells were rinsed with HBSS (Hanks Buffered Saline Solution) twice and fresh growth media was added. FIG. 21 shows the representative images of cells before and after exposure to laser. From FIG. 21(c) and FIG. 21(d), before and after irradiation, it is obvious that A549 cells labeled with GSS nanoparticles undergo thermally induced cell death when exposed to laser light. The process of laser illumination on GSS labeled cells and the effect of increase in temperature on cellular components has been studied by Raman spectroscopy. The overall process of cell death has been found to be necrotic. In this study, a Raman technique as a tool to investigate effect of rise in temperature on the cell components.

Figure 22A:
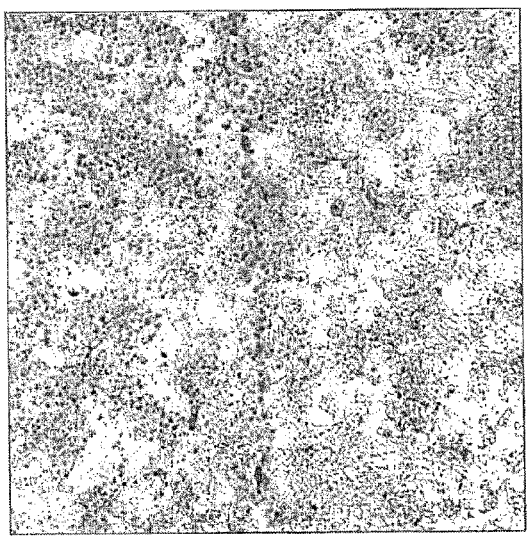
FIGS. 22A-b show cells labeled with GSS multimodal nanoparticles along a path of laser illumination (FIG. 22A) and at a higher magnification (FIG. 22B) according to an embodiment of the invention.
Figure 22B:
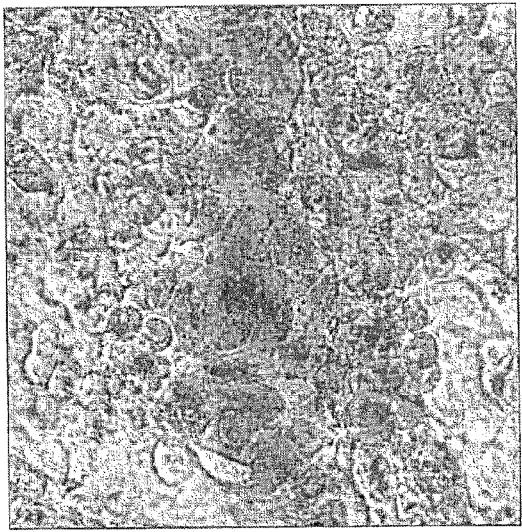

In another experiment, the effectiveness of the particles to cause possible collateral damage on surrounding cells (those not exposed to laser) was studied. The labeled cells were illuminated with Laser of (20 by 40 micron spot size) at an estimated the speed to 2.5 mm/s. After the laser scanning was finished, 200 μl of 0.4% Trypan Blue solution in phosphate buffer was added to the cells. The plate was incubated for 15 min in order for the Trypan Blue to selectively penetrate the membrane and color the dead cells. Images were taken with Olympus BX60 with an attached SPOT Insight Digital Camera, as shown in FIG. 22. The cells labeled with GSS nanoparticles falling in the path of the laser are killed selectively, as shown as a dark vertical line at the center of FIG. 22(a), which is magnified in FIG. 22(b).

Figure 23:
FIG. 23 shows a photograph of a histological section of a tumor after thermal ablation with GSS multimodal nanoparticles illuminated with 785 nm laser for 5 minutes according to an embodiment of the invention.
Figure 24:
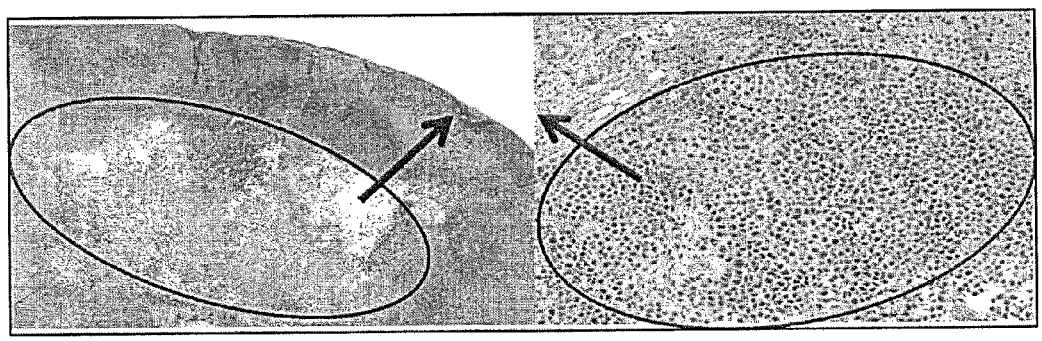
FIG. 24 shows an H and E stain of a tumor section indicating destruction of tumor cells upon illumination of GSS multimodal nanoparticles according to an embodiment of the invention.

The ability to generate heat using with NIR laser allows targeting deep tumors due to higher penetration in this region. To demonstrate the feasibility of using GSS nanoparticle for tumor hyperthermia, GSS nanoparticles were injected directly into the tumor of animal model. The tumor region was then illuminated with 785 nm laser (0.350 mA output) for duration of 5 minutes. The effect on the tumor was checked by performing the histological analysis of the tumor after sacrificing the mice. FIG. 23 shows the image from the tumor post ablation experiment. It is evident from the figure that the GSS nanoparticles caused significant damage to the tumor tissue from the heat generated due to exposure to NIR light. FIG. 24 shows the H and E stain of the tumor section.

It should be understood that the examples and embodiments described herein are for illustrative purposes only and that various modifications or changes in light thereof will be suggested to persons skilled in the art and are to be included within the spirit and purview of this application.

We claim:
1. A method for multimodal bio-imaging comprising:
providing a multimodal nanoparticle comprising a dielectric core comprising at least one oxide, a speckled metal deposition on said core where said metal deposition and said dielectric core have an interface with interpenetrated gradient, and a plurality of at least one moiety that exhibits luminescence, magnetic or paramagnetic properties, or any combination thereof, wherein said multimodal nanoparticle is a contrast agent for photo acoustic tomography (PAT) imaging and x-ray imaging, and at least one of luminescence imaging and/or magnetic resonance (MR) imaging;
introducing said multimodal nanoparticle to a desired location; and
imaging the desired location by photo acoustic tomography (PAT) imaging and at least one of magnetic resonance (MR) imaging, luminescence imaging, or x-ray imaging, wherein said multimodal nanoparticle enhances the contrast observed in said imaging, and wherein said imaging is performed simultaneously or sequentially.

2. A method of therapy comprising:
providing a multimodal nanoparticle comprising a dielectric core comprising at least one oxide, a speckled metal deposition on said core where said metal deposition and said dielectric core have an interface with interpenetrated gradient, and a plurality of at least one moiety that exhibits luminescence, magnetic or paramagnetic properties, or any combination thereof, wherein said multimodal nanoparticle is a contrast agent for photo acoustic tomography (PAT) imaging and x-ray imaging, and at least one of luminescence imaging and/or magnetic resonance (MR) imaging;
delivering said multimodal nanoparticle to a target region; and
irradiating said target region with electromagnetic radiation, wherein said multimodal nanoparticle generates heat upon absorption of said radiation, and wherein said heat is of sufficient intensity to destroy said target region.

3. The method of claim 2, wherein at least one of said at least one moiety comprises a moiety that exhibits luminescence.

4. A method of therapy comprising:
providing a multimodal nanoparticle comprising a dielectric core comprising at least one oxide, a speckled metal deposition on said core where said metal deposition and said dielectric core have an interface with interpenetrated gradient, and a plurality of at least one moiety that exhibits luminescence, magnetic or paramagnetic properties, or any combination thereof, wherein said multimodal nanoparticle is a contrast agent for photo acoustic tomography (PAT) imaging and x-ray imaging, and at least one of luminescence imaging and/or magnetic resonance (MR) imaging;
delivering said multimodal nanoparticle to a desired target region; and
irradiating said target region with neutrons, wherein said multimodal nanoparticle generates gamma-rays, X-rays and Auger electrons upon absorption of said neutrons, and wherein said emitted gamma rays, X-rays and Auger electrons are of sufficient intensity to destroy said target region.

5. The method of claim 4, wherein said multimodal particle has a moiety that exhibits luminescence.

* * * * *

UNITED STATES PATENT AND TRADEMARK OFFICE
CERTIFICATE OF CORRECTION

PATENT NO. : 8,617,522 B2
APPLICATION NO. : 13/729815
DATED : December 31, 2013
INVENTOR(S) : Parvesh Sharma et al.

It is certified that error appears in the above-identified patent and that said Letters Patent is hereby corrected as shown below:

In the Specification

Column 7,
Line 48, "MR Relaxoinetry", should read --MR Relaxometry--.
Line 60, "and a1mm slice" should read --and a 1mm slice--.

Column 8,
Line 54, "modified agle's medium" should read --modified eagle's medium--.

Column 9,
Line 27, "a1mm slice" should read --a 1 mm slice--.

Column 12,
Line 45, "100 ul" should read --100 μl--.

Signed and Sealed this
Thirteenth Day of May, 2014

Michelle K. Lee
*Deputy Director of the United States Patent and Trademark Office*